United States Patent
Song et al.

(10) Patent No.: US 9,861,908 B2
(45) Date of Patent: Jan. 9, 2018

(54) PROCESS FOR CONTINUOUS RECOVERING (METH)ACRYLIC ACID AND APPARATUS FOR THE PROCESS

(71) Applicant: LG CHEM, LTD., Seoul (KR)

(72) Inventors: Jong Hun Song, Daejeon (KR); Se Won Baek, Daejeon (KR); Sul Hee Yoo, Daejeon (KR); Yoon Jae Min, Daejeon (KR)

(73) Assignee: LG CHEM, LTD., Seoul (KR)

( * ) Notice: Subject to any disclaimer, the term of this patent is extended or adjusted under 35 U.S.C. 154(b) by 18 days.

(21) Appl. No.: 14/914,218

(22) PCT Filed: Aug. 13, 2014

(86) PCT No.: PCT/KR2014/007541
§ 371 (c)(1),
(2) Date: Feb. 24, 2016

(87) PCT Pub. No.: WO2015/030396
PCT Pub. Date: Mar. 5, 2015

(65) Prior Publication Data
US 2016/0200656 A1    Jul. 14, 2016

(30) Foreign Application Priority Data
Aug. 30, 2013 (KR) .................... 10-2013-0104121

(51) Int. Cl.
| | |
|---|---|
| *B01D 3/00* | (2006.01) |
| *B01D 11/04* | (2006.01) |
| *C07C 51/44* | (2006.01) |
| *B01D 3/40* | (2006.01) |
| *B01D 3/14* | (2006.01) |

(52) U.S. Cl.
CPC ............ *B01D 11/0488* (2013.01); *B01D 3/00* (2013.01); *B01D 3/143* (2013.01); *B01D 3/40* (2013.01); *B01D 11/04* (2013.01); *C07C 51/44* (2013.01)

(58) Field of Classification Search
CPC ....... C07C 51/44; B01D 3/00; B01D 11/0488; B01D 11/04
See application file for complete search history.

(56) References Cited

U.S. PATENT DOCUMENTS

| | | |
|---|---|---|
| 5,811,574 A | 9/1998 | Exner et al. |
| 5,897,749 A | 4/1999 | Kroker et al. |
| 5,900,125 A | 5/1999 | Exner et al. |
| 2015/0203431 A1 | 7/2015 | Baek et al. |

FOREIGN PATENT DOCUMENTS

| | | | |
|---|---|---|---|
| EP | 0023774 A1 | * | 2/1981 |
| JP | 07-031803 A | | 2/1995 |
| JP | 07031803 A | * | 2/1995 |
| JP | 2008-506653 A | | 3/2008 |
| JP | 4084993 A | | 4/2008 |
| JP | 2009263348 A | | 11/2009 |
| KR | 10-1997-0015558 A | | 4/1997 |
| KR | 10-0349602 B1 | | 11/2002 |
| KR | 10-0371759 B1 | | 5/2003 |
| KR | 10-0464841 B1 | | 12/2004 |
| KR | 10-2010-0107029 A | | 10/2010 |
| KR | 10-2009-0041355 A | | 2/2011 |
| KR | 10-1011769 A | | 2/2011 |
| WO | 2013/037134 A1 | | 3/2013 |

* cited by examiner

*Primary Examiner* — Paul A Zucker
(74) *Attorney, Agent, or Firm* — Dentons US LLP (57) ABSTRACT

This disclosure relates to a method of continuous recovery of (meth)acrylic acid and an apparatus used for the recovery method. The method of continuous recovery of (meth) acrylic acid according to the present invention may effectively remove scum, thus enabling stable operation of the continuous process.

10 Claims, 5 Drawing Sheets

PROCESS FOR CONTINUOUS RECOVERING (METH)ACRYLIC ACID AND APPARATUS FOR THE PROCESS

This application is a National Stage Entry of International Application No. PCT/KR2014/007541, filed Aug. 13, 2014, and claims the benefit of and priority to Korean Application Nos. 10-2013-0104121, filed on Aug. 30, 2013, all of which are hereby incorporated by reference in their entirety for all purposes as if fully set forth herein.

TECHNICAL FIELD

The present invention relates to a method of continuous recovery of (meth)acrylic acid and an apparatus for the method.

BACKGROUND OF ART (Meth)acrylic acid is generally prepared by gas phase oxidation of propane, propylene, (meth)acrolein, and the like in the presence of a catalyst. For example, propane, propylene, and the like are converted to (meth)acrylic acid through (meth)acrolein by gas phase oxidation in the presence of an appropriate catalyst in a reactor, and a reaction product mixed gas including (meth)acrylic acid, non-reacted propane or propylene, (meth)acrolein, an inert gas, carbon dioxide, water vapor, and various organic by-products (acetic acid, heavies, and the like) is obtained in the back end of the reactor.

The (meth)acrylic acid-containing mixed gas contacts an absorption solvent including water in a (meth)acrylic acid absorption tower, and is recovered as a (meth)acrylic acid aqueous solution. Further, (meth)acrylic acid-stripped insoluble gas is recycled for a synthesis reaction of (meth)acrylic acid, and a part thereof is incinerated, converted into harmless gas, and discharged. The (meth)acrylic acid aqueous solution is extracted, distilled, and purified to obtain (meth)acrylic acid.

Various methods of controlling process conditions or a process sequence and the like to improve the recovery efficiency of (meth)acrylic acid have been suggested. Representatively, as a method for separating water and acetic acid from the (meth)acrylic acid aqueous solution obtained in the (meth)acrylic acid absorption tower, an azeotropic distillation method using a hydrophobic solvent in a distillation column is known. Further, a method of supplying a (meth)acrylic acid aqueous solution to an extraction column to obtain a (meth)acrylic acid extract solution with reduced water content and a raffinate solution thereof, and distilling the extract, thereby reducing energy consumption amount, is known.

Meanwhile, in the (meth)acrylic acid aqueous solution obtained in the (meth)acrylic acid absorption tower, in addition to (meth)acrylic acid, various organic by-products such as maleic acid, terephthalic acid, aldehyde, and (meth)acrylic acid polymer are included. In addition, due to the properties of a continuous process for recovering (meth)acrylic acid, scum is formed due to poorly water-soluble materials in the organic by-products. The scum contaminates a (meth)acrylic acid recovery apparatus, and is particularly accumulated in an extraction column to decrease recovery efficiency of (meth)acrylic acid.

DETAILED DESCRIPTION OF THE INVENTION

Technical Problem

It is an object of the present invention to provide a method for continuous recovery of (meth)acrylic acid that may more effectively remove scum produced in the continuous recovery process of (meth)acrylic acid, thus enabling stable operation of the continuous process.

It is another object of the present invention to provide an apparatus that can be used for the method for continuous recovery of (meth)acrylic acid.

Technical Solution

According to the present invention, a method of continuous recovery of (meth)acrylic acid is provided, including:

an extraction process wherein a (meth)acrylic acid aqueous solution is contacted with an extraction solvent in an extraction column to obtain a (meth)acrylic acid extract solution through the upper outlet of the extraction column, and obtain a raffinate solution that passes through the lower stationary section of the extraction column through the lower outlet; and a distillation process wherein a feed containing the (meth)acrylic acid extract solution is distilled to obtain (meth)acrylic acid, wherein the raffinate solution containing scum that is accumulated at the interface between an organic phase and an aqueous phase formed by phase separation of the raffinate solution in the lower stationary section of the extraction column is discharged through a side stream equipped at any one point of the lower stationary section and filtered, and the filtrate is inflowed through a side stream equipped at any other point of the lower stationary section.

The extraction process may be conducted such that the interface between an organic phase and an aqueous phase by phase separation of the raffinate solution may be formed at a location of the side stream equipped at any one point of the lower stationary section of the extraction column.

The discharging of the raffinate solution containing scum and the filtering through the side streams of the extraction column may be conducted continuously or discontinuously.

The outflow direction of the raffinate solution containing scum through the side stream of the extraction column and the inflow direction of the filtrate through the side stream of the extraction column may be opposite to each other.

The filtering may be conducted using a filter having pores with an average diameter of 50 μm or less.

Besides the filtering through the side stream of the extraction column, a step of filtering a raffinate solution obtained through the lower outlet of the extraction column may be further conducted.

Meanwhile, according to the present invention, an apparatus for continuous recovery of (meth)acrylic acid is provided, including:

a (meth)acrylic acid absorption tower (100) equipped with a mixed gas inlet into which a mixed gas including (meth)acrylic acid, organic by-products, and vapor, which is produced by a synthesis reaction of (meth)acrylic acid, is fed, and a (meth)acrylic acid aqueous solution outlet from which a (meth)acrylic acid aqueous solution obtained by contact of the mixed gas with an absorption solvent including water is discharged;

a (meth)acrylic acid extraction column (200) equipped with a (meth)acrylic acid aqueous solution inlet connected with the (meth)acrylic acid aqueous solution outlet of the absorption tower (100) through an aqueous solution transfer line (102), an extract outlet from which the (meth)acrylic acid extract obtained by contact of the inflowed (meth)acrylic acid aqueous solution with an extraction solvent is discharged, a lower stationary section in which a raffinate solution obtained by contact of the (meth)acrylic aqueous solution with an extraction solvent remains stationary, a raffinate outlet from which the raffinate solution passing through the lower stationary section is discharged, a scum outlet port where at least a part of the raffinate solution containing scum is discharged through a side stream equipped at any one point of the lower stationary section, and a filtrate inlet port formed such that a filtrate obtained through filtering of the raffinate solution discharged from the scum outlet port is inflowed through a side stream equipped at any other point of the lower stationary section;

a side filtering system (220) equipped with a raffinate inlet connected with the scum outlet port of the extraction column (200), into which the raffinate containing scum is inflowed, a filter for filtering the inflowed raffinate solution, a scum outlet from which the scum separated from the raffinate solution by filtering is discharged, and a filtrate outlet connected such that the filtrate is fed to the filtrate inlet port of the extraction column; and a distillation column (300) equipped with an extract inlet connected with the extract outlet of the extraction column (200) through an extract transfer line (203), and a (meth) acrylic acid outlet from which (meth)acrylic acid obtained by distillation of a feed containing the inflowed extract solution is discharged.

Advantageous Effects

The method of continuous recovery of (meth)acrylic acid according to the present invention may effectively remove scum formed in the continuous recovery process of (meth) acrylic acid, thus enabling more stable operation of the continuous process.

REFERENCE NUMERALS

1: (meth)acrylic acid containing mixed gas
100: (meth)acrylic acid absorption tower
102: (meth)acrylic acid aqueous solution transfer line
150: acetic acid absorption tower
200: (meth)acrylic acid extraction column
201: filtrate transfer line
203: extract transfer line
220: side filtering system
221: scum outlet port
229: filtrate inlet port
250: lower filtering system
300: distillation column
350: phase separation tank
400: heavies separation tower
CAA: crude (meth)acrylic acid
HPAA: high purity (meth)acrylic acid

DETAILED DESCRIPTION OF THE EMBODIMENTS

Hereinafter, a method of continuous recovery of (meth) acrylic acid and a recovery apparatus according to the embodiments of the invention will be explained.

First, the technical terms used herein are only to mention specific embodiments, and are not intended to limit the invention, and singular forms used herein include plural forms, unless they have clearly opposite meanings. Further, the meaning of 'comprising' as used herein embodies a specific property, area, integer, step, operation, element, or component, and it does not exclude the addition of other specific properties, areas, integers, steps, operations, elements, or components.

Unless otherwise described, terms used herein are defined as follows.

The term '(meth)acrylic acid' generally refers to acrylic acid, methacrylic acid, or a mixture thereof.

Further, the term '(meth)acrylic acid-containing mixed gas' generally refers to a mixed gas that may be produced when (meth)acrylic acid is prepared by gas phase oxidation. As a non-limiting example, the (meth)acrylic acid-containing mixed gas may be obtained by gas phase oxidation of at least one compound selected from the group consisting of propane, propylene, butane, i-butylene, t-butylene, and (meth)acrolein ('raw material compound') in the presence of a catalyst, wherein the (meth)acrylic acid-containing mixed gas may include (meth)acrylic acid, non-reacted raw material compounds, (meth)acrolein, an inert gas, carbon monoxide, carbon dioxide, water vapor, and various organic by-products (acetic acid, heavies, and the like), and the like. Herein, a poorly water-soluble floating material formed by the organic by-products is referred to as 'scum'.

The term '(meth)acrylic acid aqueous solution' refers to an aqueous solution containing (meth)acrylic acid, and for example, it may be obtained by contacting the (meth)acrylic acid-containing mixed gas with an absorption solvent containing water.

The term 'feed' in an extraction process refers to a liquid mixture containing a solute to be extracted, and it may be a mixture of a solute that is soluble in an extraction solvent and an inert material that is not soluble in an extraction solvent. Herein, if the extraction solvent is added to the feed, the solute is dissolved in the extraction solvent from the feed by mass transfer. Thereby, the extraction solvent in which a significant amount of solutes is dissolved forms an extract solution, and the feed that is deprived of a significant amount of solutes forms a raffinate solution.

Meanwhile, in liquid-liquid extraction using agitated columns such as a Karr-type column and a Scheibel-type column, a relatively light phase is fed to the lower stage of the extraction column, and a relatively heavy phase is fed to the upper stage of the extraction column. Further, extraction is progressed by the contact of materials fed to the extraction column, to obtain a light phase and a heavy phase of new compositions.

The light phase of a new composition obtained through the extraction process is obtained through the upper outlet of the extraction column, and the heavy phase of a new composition is obtained through the lower outlet of the extraction column. In general, the heavy phase of the new composition obtained through the extraction process, before being discharged to the lower outlet of the extraction column, remains stationary at the lower part of the extraction column, and a part thereof is discharged to the lower outlet of the extraction column. Herein, the section of the extraction column in which the heavy phase remains stationary is referred to as 'lower stationary section' (or 'stationary section of heavy phase').

For example, in the process of extracting (meth)acrylic acid included in a (meth)acrylic acid aqueous solution using an extraction solvent, the (meth)acrylic acid aqueous solution that is in a relatively heavy phase is fed to the upper stage of the extraction column, and the extraction solvent that is in a relatively light phase is fed to the lower stage of the extraction column. Further, extraction is progressed by the contact thereof, an extract solution in which a significant amount of (meth)acrylic acid is dissolved and a raffinate solution that is deprived of a significant amount of (meth) acrylic acid are obtained. Herein, the extract solution that is in a relatively light phase is obtained through the upper outlet of the extraction column, and the raffinate solution that is in a relatively heavy phase is obtained through the lower outlet of the extraction column.

The raffinate solution, before being discharged to the lower outlet of the extraction column, remains stationary at the lower section of the extraction column, and a part thereof is discharged to the lower outlet of the extraction column. The section of the extraction column in which the raffinate solution remains stationary is referred to as 'lower stationary section' (or 'stationary section of raffinate solution'). Further, in the raffinate solution, an organic phase and an aqueous phase exist together, and the raffinate solution may be separated into an organic phase and an aqueous phase and form an interface in the lower stationary section according to process conditions.

With regard to filtering in the extraction process, among the main stream of the extraction column (namely, upper discharge flow or lower discharge flow of the extraction column), a filtering method for the lower discharge flow is referred to as 'lower filtering', and the means for conducting the lower filtering is referred to as 'lower filtering system'. Further, besides the main stream of the extraction column, a filtering method for side stream discharge flow is referred to as 'side filtering', and the means for conducting the side filtering is referred to as 'side filtering system'.

Hereinafter, referring to the attached drawings, specific embodiments of the invention will be explained in detail so that one of ordinary knowledge in the art may easily practice it. However, the present invention may be embodied in various forms, and is not limited to the examples.

In general, in the synthesis process of (meth)acrylic acid, various organic by-products are produced together with (meth)acrylic acid, and scum is formed by poorly water-soluble substances included in the organic by-products. Due to the characteristic of a continuous process, scum contaminates the inside of various apparatuses, thus making stable process operation impossible, and lowers the recovery rate of (meth)acrylic acid.

In this regard, the inventors have suggested a method of continuous recovery of (meth)acrylic acid including an absorption process, an extraction process, and a distillation process, wherein the lower discharged material (raffinate solution) of the extraction column is filtered to remove scum, and the filtrate is used as an absorption solvent of the absorption process.

However, according to the study results of the inventors, it was confirmed that the lower filtering can remove only a part of scum included in the raffinate solution, and thus, as the operation time elapses, scum is accumulated inside the extraction column. Namely, scum is accumulated in the stationary section of a raffinate solution of the lower part of the extraction column (particularly, at the interface of the organic phase and the aqueous phase formed in the stationary section) while forming a layer, and as the operation time elapses, the thickness of accumulated scum increases from the interface respectively toward the direction of the organic phase and the direction of the aqueous phase.

However, the previously suggested lower filtering selectively recovers and filters only the aqueous phase formed in the stationary section of the lower part of the extraction column, so as to use the filtrate as an absorption solvent of the absorption process of (meth)acrylic acid. Thus, according to the lower filtering, scum accumulated close to the aqueous phase can be removed, but scum accumulated close to the organic phase cannot be removed and remains. Thus, as the operation time elapses, scum is accumulated toward the direction of the organic phase, and finally, shutdown of the extraction column becomes inevitable.

Thus, the inventors confirmed during repeated studies for ameliorating these problems that if scum that is accumulated at the interface between an organic phase and an aqueous phase formed by separation of the raffinate solution in the lower stationary section of the extraction column is discharged through a side stream equipped at any one point of the lower stationary section of the extraction column and filtered, and the filtrate is inflowed again into the lower stationary section of the extraction column (side filtering method), scum accumulated close to the organic phase as well as scum accumulated close to the aqueous phase at the interface may be effectively removed.

I. A Method of Continuous Recovery of (Meth)Acrylic Acid

According to one embodiment of the invention, a method of continuous recovery of (meth)acrylic acid is provided, including:

an extraction process wherein a (meth)acrylic acid aqueous solution is contacted with an extraction solvent in an extraction column to obtain a (meth)acrylic acid extract solution through the upper outlet of the extraction column, and obtain a raffinate solution that passes through the lower stationary section of the extraction column through the lower outlet; and a distillation process wherein a feed containing the (meth)acrylic acid extract solution is distilled to obtain (meth)acrylic acid, wherein the raffinate solution containing scum that is accumulated at the interface between an organic phase and an aqueous phase formed by phase separation of the raffinate solution in the lower stationary section of the extraction column is discharged through a side stream equipped at any one point of the lower stationary section and filtered, and the filtrate is inflowed through a side stream equipped at any other point of the lower stationary section.

Basically, the method of continuous recovery of (meth)acrylic acid according to the present invention includes an extraction process of a (meth)acrylic acid aqueous solution and a distillation process, and particularly, scum accumulated in the lower stationary section in the extraction process may be more effectively removed by side filtering.

According to one embodiment of the invention, the method of continuous recovery of (meth)acrylic acid includes: an absorption process wherein a mixed gas including (meth)acrylic acid, organic by-products, and vapor, which is produced by a synthesis reaction of (meth)acrylic acid, is contacted with an absorption solvent including water to obtain a (meth)acrylic acid aqueous solution; an extraction process wherein the (meth)acrylic acid aqueous solution obtained through the absorption process is contacted with an extraction solvent in an extraction column to obtain a (meth)acrylic acid extract solution through the upper outlet of the extraction column and a raffinate solution through the lower outlet of the extraction column; and a distillation process wherein a feed including the (meth)acrylic acid extract obtained through the extraction process is distilled to obtain (meth)acrylic acid. The method of continuous recovery of (meth)acrylic acid according to the embodiment may be conducted using the apparatus shown in FIG. 1.

According to another embodiment of the invention, the method of continuous recovery of (meth)acrylic acid may include: the absorption process for obtaining a (meth)acrylic acid aqueous solution; an extraction process wherein a part of the (meth)acrylic acid aqueous solution obtained through the absorption process is contacted with an extraction solvent in an extraction column to obtain a (meth)acrylic acid extract solution through the upper outlet of the extraction column and a raffinate solution through the lower outlet of the extraction column; and a distillation process wherein a feed containing the remainder of the (meth)acrylic acid aqueous solution obtained through the absorption process and the (meth)acrylic acid extract solution obtained through the extraction process is distilled to obtain (meth)acrylic acid. The method of continuous recovery of (meth)acrylic acid according to the embodiment may be conducted using the apparatus shown in FIG. 2.

Figure 1:
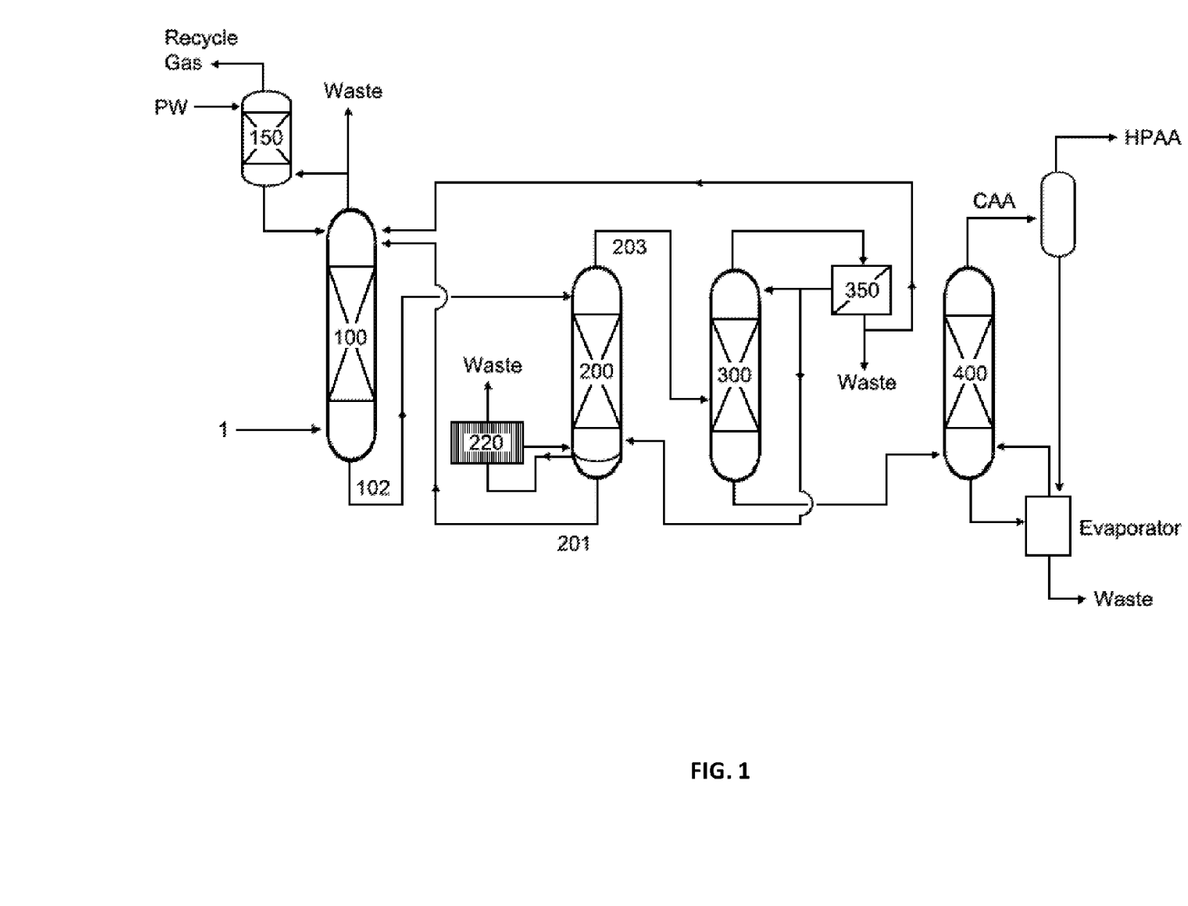
FIG. 1 illustrates a method of continuous recovery of (meth)acrylic acid according to a first inventive embodiment of this application, and the apparatus used therein.
Figure 2:
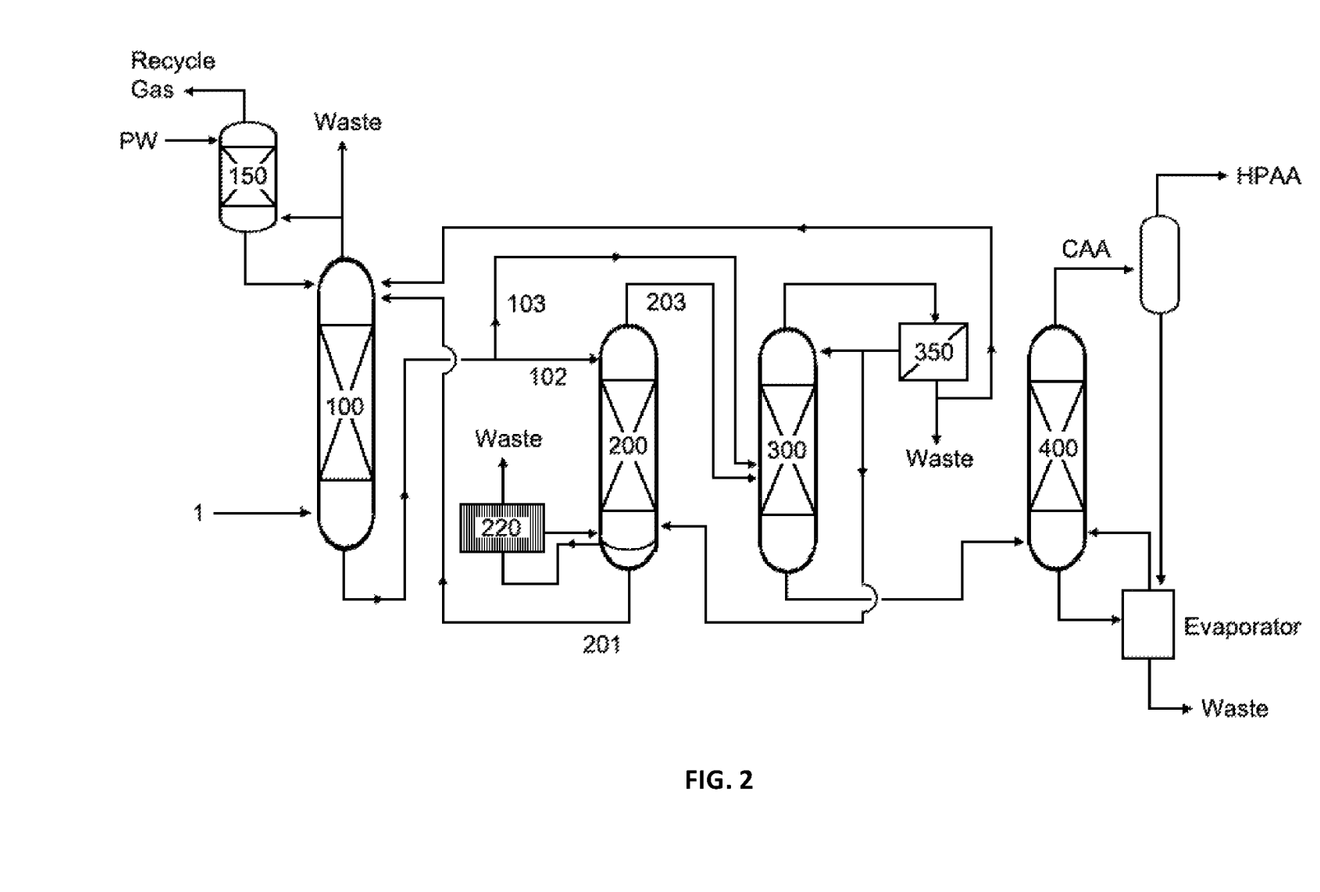
FIG. 2 illustrates a method of continuous recovery of (meth)acrylic acid according to a second inventive embodiment of this application, and the apparatus used therein.
Figure 4:
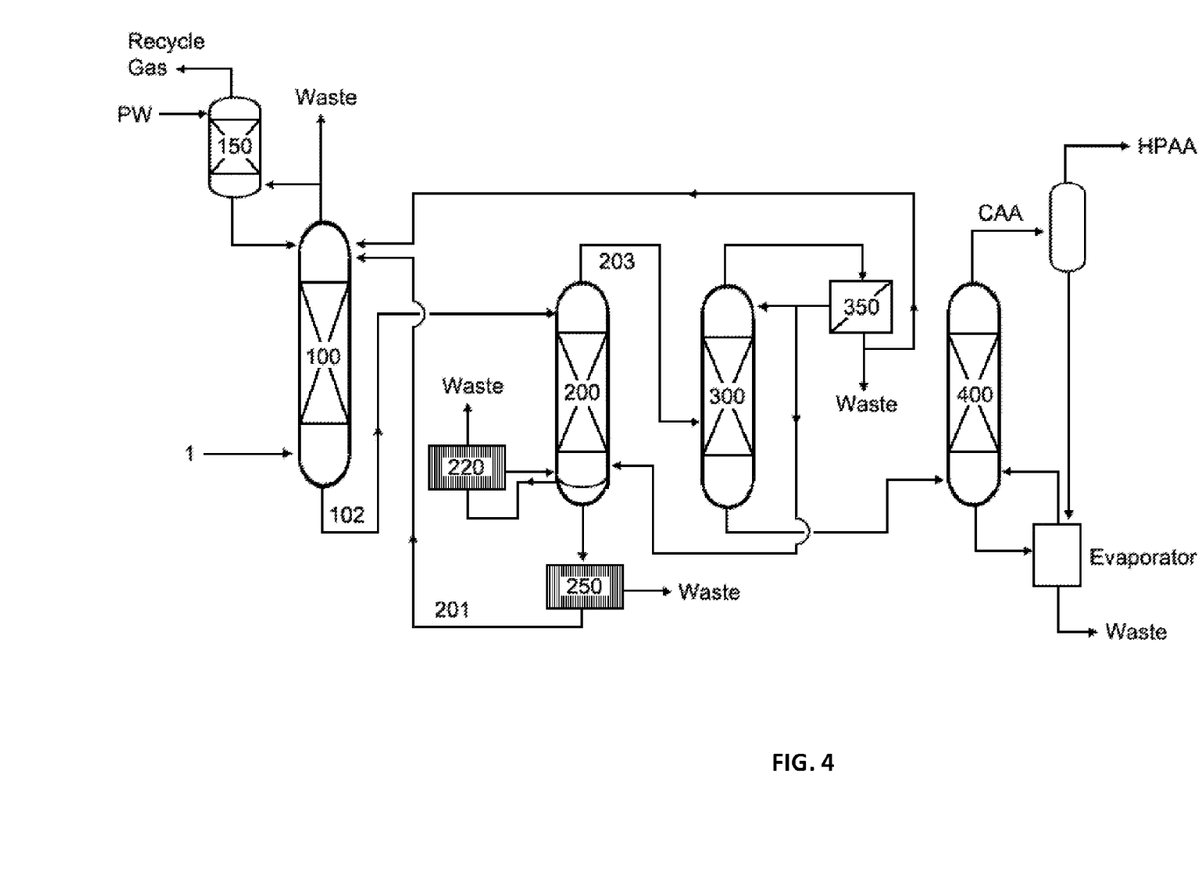
FIG. 4 illustrates additional apparatus used in the method of continuous recovery of (meth)acrylic acid according to the first inventive embodiment of this application.
Figure 5:
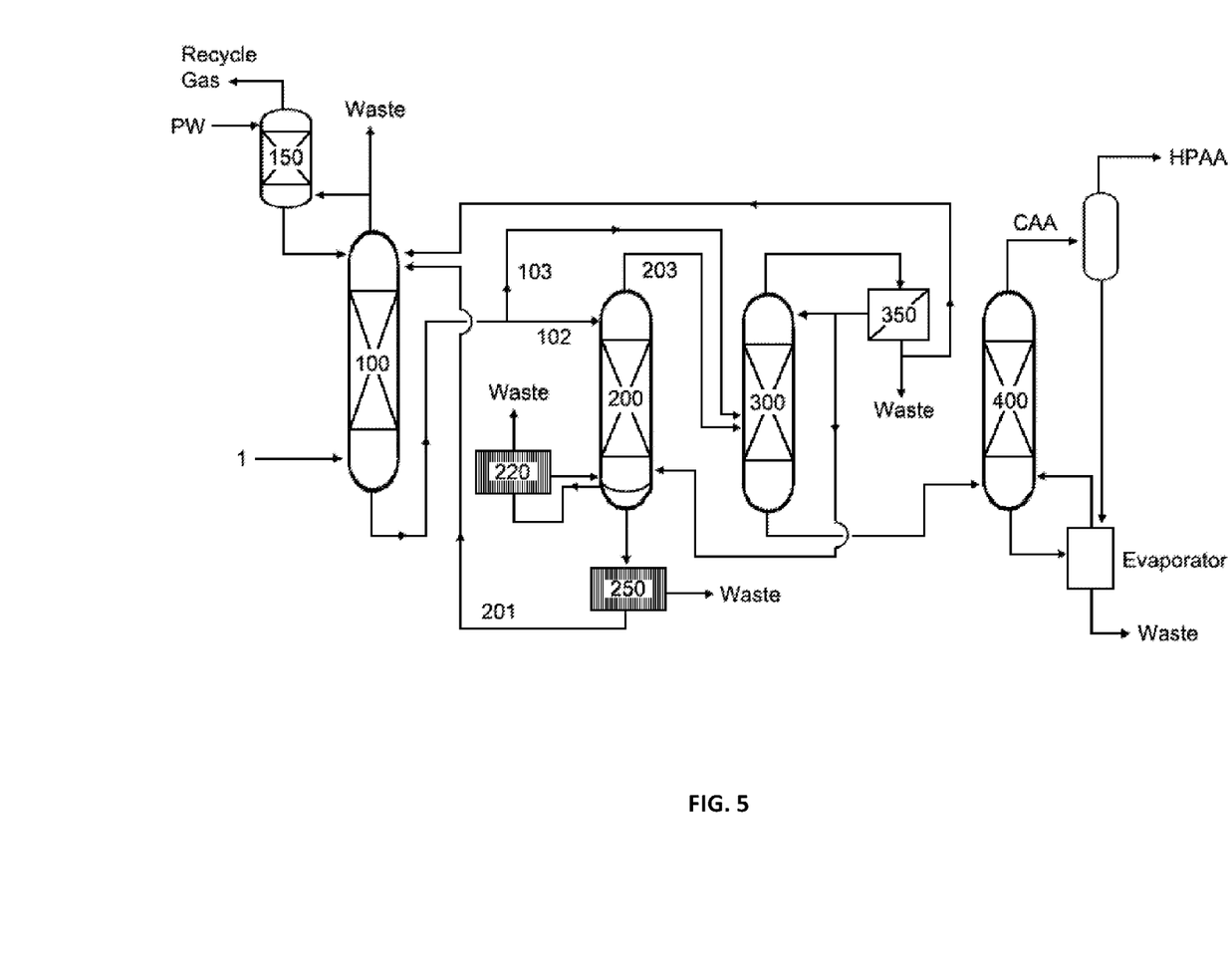
FIG. 5 illustrates additional apparatus used in the method of continuous recovery of (meth)acrylic acid according to the second inventive embodiment of this application.

According to another embodiment of the invention, the method of continuous recovery of (meth)acrylic acid may further include a step of filtering the raffinate solution obtained from the lower outlet of the extraction column in each embodiment according to FIG. 1 or FIG. 2, as shown in FIG. 4 and FIG. 5.

Hereinafter, referring to FIG. 1 and FIG. 2, each process that can be included in the embodiments of the invention will be explained.

(Absorption Process)

An absorption process is a process for obtaining a (meth)acrylic acid aqueous solution, and it may be conducted by contacting a (meth)acrylic acid-containing mixed gas obtained through the synthesis reaction of (meth)acrylic acid with an absorption solvent including water.

As a non-limiting example, the synthesis reaction of (meth)acrylic acid may be conducted by the oxidation reaction of at least one compound selected from the group consisting of propane, propylene, butane, isobutylene, and (meth)acrolein in the presence of a gas phase catalyst. Herein, the gas phase oxidation reaction may be progressed using a gas phase oxidation reactor of a common structure and under common reaction conditions. As the catalyst for the gas phase oxidation reaction, common catalysts may be used, and for example, catalysts suggested in Korean Registered Patent No. 0349602 and No. 037818, and the like may be used. In the (meth)acrylic acid-containing mixed gas produced by the gas phase oxidation reaction, in addition to the desired product (meth)acrylic acid, non-reacted raw material compounds, intermediate (meth)acrolein, an inert gas, carbon dioxide, vapor, and various organic by-products (acetic acid, light ends, heavies, and the like) may be included.

Further, referring to FIG. 1, the (meth)acrylic acid aqueous solution may be obtained by feeding a (meth)acrylic acid-containing mixed gas (1) to a (meth)acrylic acid absorption tower (100), so as to contact it with an absorption solvent including water.

Herein, the kind of the (meth)acrylic acid absorption tower (100) may be determined considering contact efficiency of the mixed gas (1) with the absorption solvent and the like. As non-limiting examples, the (meth)acrylic acid absorption tower (100) may be a packed tower or a multi-stage tray tower. Inside the packed tower, filler such as a Raschig ring, a pall ring, a saddle, gauze, structured packing, and the like may be applied.

Further, considering the efficiency of the absorption process, the mixed gas (1) may be fed to the lower part of the absorption tower (100), and the solvent including water may be fed to the upper part of the absorption tower (100).

The absorption solvent may include water such as tap water, deionized water, and the like, and it may include recycled process water introduced from other processes (for example, an aqueous phase recycled from an extraction process and/or a distillation process). In the absorption solvent, a trace amount of organic by-products introduced from other processes (for example, acetic acid) may be included. However, considering the absorption efficiency of (meth)acrylic acid, it is preferable that organic by-products are included in the content of 15 wt % or less in the absorption solvent fed to the absorption tower (100) (particularly, in the recycled process water).

According to the embodiment of the invention, a raffinate solution obtained in a (meth)acrylic acid extraction column (200) may be recycled to the absorption tower (100) and used as an absorption solvent. Herein, it may be advantageous in terms of improvement in process efficiency that the raffinate solution is fed to the upper part of the absorption tower (100).

The (meth)acrylic acid absorption tower (100) may be operated at an internal pressure of 1 to 1.5 bar or 1 to 1.3 bar, and at an internal temperature of 50 to 100° C. or 50 to 80° C., considering condensation conditions and moisture content according to saturated water vapor pressure, and the like.

Meanwhile, through the absorption process, a (meth)acrylic acid aqueous solution is discharged to the lower part of the (meth)acrylic acid absorption tower (100), and (meth)acrylic acid-stripped non-condensable gas is discharged to the upper part thereof. Herein, it may be favorable in terms of the efficiency of the total process that 40 wt % or more, or 40 to 90 wt %, or 50 to 90 wt %, or 50 to 80 wt % of (meth)acrylic acid may be included in the (meth)acrylic acid aqueous solution.

The obtained (meth)acrylic acid aqueous solution, as shown in FIG. 1, may be fed to the (meth)acrylic acid extraction column (200) through an aqueous solution transfer line (102). Further, the obtained (meth)acrylic acid aqueous solution, as shown in FIG. 2, may be divided and fed to the (meth)acrylic acid extraction column (200) and a distillation column (300) through aqueous solution transfer lines (102 and 103).

As shown in FIG. 1, if an extraction process is introduced between a (meth)acrylic acid absorption process and a distillation process, most absorption solvent included in the (meth)acrylic acid aqueous solution may be removed in the extraction process, thus lowering the treatment load of the distillation process, and reducing energy consumption.

As shown in FIG. 2, if an extraction process is introduced between a (meth)acrylic acid absorption process and a distillation process, and simultaneously a (meth)acrylic acid aqueous solution is divided and fed to the extraction process and the distillation process, the distillation process may be operated under more relaxed operation conditions than the process as shown in FIG. 1. Herein, the ratio of the (meth)acrylic acid aqueous solution divided and fed to the extraction column (200) and the distillation column (300) may be determined considering capacity of each column, treatment performance, energy efficiency improvement effect, and the like. According to one embodiment, it may be favorable for manifestation of the above-explained effect that 5 to 70 wt %, or 10 to 60 wt %, or 10 to 50 wt % of the (meth)acrylic acid aqueous solution may be fed to the extraction column (200), and the remainder may be fed to the distillation column (300).

Meanwhile, at least a part of the non-condensable gas discharged to the upper part of the (meth)acrylic acid absorption tower (100) may be fed to a process of recovering organic by-products (particularly, acetic acid) included in the non-condensable gas, and the remainder may be fed to a waste gas incinerator and discarded. Namely, according to one embodiment of the invention, a process of contacting the non-condensable gas with an absorption solvent to recover acetic acid included in the non-condensable gas may be progressed.

The process of contacting the non-condensable gas with an absorption solvent may be conducted in an acetic acid absorption tower (150). As a non-limiting example, an absorption solvent (process water) for absorbing acetic acid may be fed to the upper part of the acetic acid absorption tower (150), and an aqueous solution containing acetic acid may be discharged to the lower part of the acetic acid absorption tower (150). Further, the acetic acid-containing aqueous solution may be fed to the upper part of the (meth)acrylic acid absorption tower (100) and used as an absorption solvent, and acetic acid-stripped non-condensable gas may be recycled to the synthesis process of (meth)acrylic acid and reused.

Herein, for effective absorption of acetic acid, the acetic acid absorption tower (150) may be operated at the internal pressure of 1 to 1.5 bar, or 1 to 1.3 bar, and at the internal temperature of 50 to 100° C. or 50 to 80° C. In addition, specific operation conditions of the acetic acid absorption tower (150) may follow the disclosure of Korean Laid-Open Patent Publication No. 2009-0041355.

(Extraction Process)

An extraction process wherein a (meth)acrylic acid aqueous solution is contacted with an extraction solvent in an extraction column to obtain a (meth)acrylic acid extract solution and a raffinate solution thereof is conducted. Herein, the (meth)acrylic acid aqueous solution may be prepared by the above-explained absorption process.

The extraction process may be conducted in a (meth)acrylic acid extraction column (200). The (meth)acrylic acid aqueous solution fed to the extraction column (200) contacts an extraction solvent, and is discharged as an extract solution in which a significant amount of (meth)acrylic acid is dissolved and a raffinate solution that is deprived of a significant amount of (meth)acrylic acid, respectively. Herein, the extraction solution that is in a relatively light phase is obtained through the upper outlet of the extraction column (200), and the raffinate solution that is in a relatively heavy phase is obtained through the lower outlet of the extraction column. Before the raffinate solution is discharged from the extraction column (200), a certain amount thereof remains stationary in the stationary section of the lower part of the extraction column, and a part thereof is discharged to the lower outlet of the extraction column.

As such, by contacting the (meth)acrylic acid aqueous solution with an extraction solvent in an extraction column (200) (namely, extraction with small energy consumption compared to distillation), most water included in the (meth) acrylic acid aqueous solution may be removed. Thereby, the treatment load of the subsequent distillation process may be lowered, thus improving energy efficiency of the total process. Furthermore, by lowering the treatment load of the distillation process, polymerization of (meth)acrylic acid that may be generated during distillation may be minimized, to secure more improved recovery efficiency of (meth) acrylic acid.

Meanwhile, in the extraction process, at the lower stationary section of the extraction column (200), a certain amount of a raffinate solution remains stationary and exists while being phase separated into an organic phase and an aqueous phase. Further, as the production amount of a raffinate solution by the extraction and the discharged amount of a raffinate solution through the lower outlet are maintained substantially the same, the amount of a raffinate solution that remains stationary at the lower part of the extraction column (200) and the interface between the organic phase and the aqueous phase are maintained at a constant level.

However, as the operation of the extraction column is continued, scum is accumulated at the interface between the organic phase and the aqueous phase due to the raffinate solution that remains stationary at the lower part of the extraction column. The scum is accumulated while forming a layer on the interface between the organic phase and the aqueous phase formed in the stationary section of the lower part of the extraction column, and as the operation time elapses, the thickness of accumulated scum increases from the interface respectively toward the organic phase direction and the aqueous phase direction. However, since the scum contaminates various apparatuses, and particularly is accumulated at the extraction column to lower the recovery rate of (meth)acrylic acid, it is preferable to remove scum for stable process operation.

With regard to removal of the scum, the inventors have suggested a method of removing scum by filtering a raffinate solution discharged to the lower part of the extraction column (200), and using the filtrate as an absorption solvent of an absorption process. However, according to the previously suggested method, among the scum accumulated at the interface between the organic phase and the aqueous phase, the scum close to the aqueous phase may be removed, but the scum close to the organic phase may not be removed and remains inside the extraction column. Thus, in the case of the previously suggested method, as the operation time elapses, scum is accumulated inside the extraction column, and finally, shutdown of the extraction column becomes inevitable.

However, the method of continuous recovery of (meth) acrylic acid according to one embodiment of the invention uses side filtering, wherein a raffinate solution containing scum accumulated at the interface between an organic phase and an aqueous phase formed in the lower stationary section of the extraction column (200) is discharged through a side stream equipped at any one point of the lower stationary section and filtered, and the filtrate is inflowed again through a side stream equipped at any other point of the lower stationary section.

Namely, as shown in FIG. 1 or FIG. 2, the side filtering is a method of discharging the raffinate solution containing scum accumulated at the interface between an organic phase and an aqueous phase using a pump through a side stream equipped at any one point of the lower stationary section of the extraction column (200), filtering it through a side filtering system (220) to remove scum from the raffinate solution, and then introducing the filtrate again into the lower stationary section of the extraction column through a side stream equipped at any other point of the lower stationary section. Thereby, the side filtering may more effectively remove even scum accumulated close to the organic phase at the interface, which was difficult to remove by the previous lower filtering.

The side filtering is a method of recovering a part of the raffinate solution that remains stationary at the lower part of the extraction column (200) (particularly, a certain amount of the raffinate solution including the interface between the organic phase and the aqueous phase) through a side stream equipped at the lower stationary section of the extraction column (200). Thus, it is advantageous that the interface between the organic phase and the aqueous phase formed by phase separation of the raffinate solution is maintained at a constant level, so as to conduct the side filtering with higher efficiency. Preferably, the extraction process may be conducted such that the interface between the organic phase and the aqueous phase by phase separation may be formed at a location of the side stream equipped at any one point of the lower stationary section of the extraction column. Herein, the location at which the interface is formed may be controlled through the production amount of the raffinate solution by extraction and the discharge amount of the raffinate solution through the lower outlet of the extraction column (200).

Further, the discharging of the raffinate solution containing scum and the filtering through the side streams of the extraction column may be conducted continuously or discontinuously. Namely, the side filtering may be continuously conducted over the whole extraction process, or it may be discontinuously conducted according to the amount of scum accumulated at the interface.

Meanwhile, since scum has high viscosity and adheres together, if the discharge mass flow through the side stream of the extraction column (200) is low, scum may not be smoothly discharged. In this regard, according to the study result of the inventors, the discharge efficiency of scum through the side stream of the extraction column (200) may vary according to the location of a port connecting the extraction column (200) and the side filtering system (220). Namely, scum removal efficiency may vary according to the outflow direction of the raffinate solution containing scum through the side stream of the extraction column (200) and the inflow direction of the filtrate through the side stream of the extraction column (200).

Figure 3:
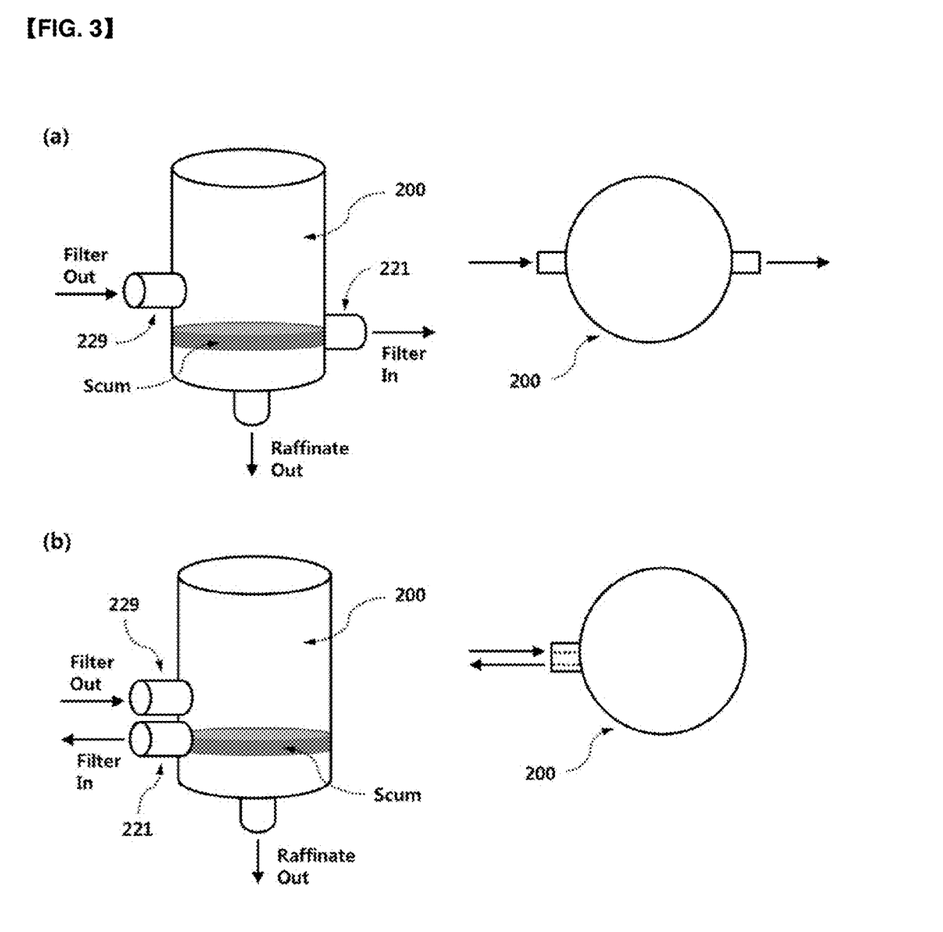
FIGS. 3(a) and 3(b) illustrate the direction of flow of scum according to exemplary embodiments of this application.

According to one embodiment, as shown in FIG. 3 (*a*), in case the outflow direction of scum (Filter In) through the side stream of the extraction column (200) and the inflow direction (Filter Out) of the filtrate into the extraction column (200) are identical, scum may be accumulated around a filtrate inlet port (229) by a fluid mechanical principle, and scum discharge efficiency through a scum outlet port (221) may relatively decrease. To the contrary, as shown in FIG. 3 (*b*), in case the outflow direction of scum (Filter In) through the side stream of the extraction column (200) and the inflow direction (Filter Out) of the filtrate into the extraction column (200) are opposite to each other, scum may be discharged more smoothly due to the flow of filtrate through the filtrate inlet port (229).

That is to say, compared to the case wherein the scum outlet port (221) and the filtrate inlet port (229) of the extraction column (200) make an angle of 180° as shown in the right drawing of FIG. 3 (*a*), the case wherein the angle is less than 180°, less than 135°, or less than 90°, or less than 45°, or 0° as shown in the right drawing of FIG. 3 (*b*) may be favorable for smooth discharge of scum.

Herein, considering that an organic phase and an aqueous phase may be included in the discharged substance through the scum outlet port (221) and the introduced substance through the filtrate inlet port (229), and for smooth phase separation of the organic phase and the aqueous phase in the lower stationary section of the extraction column, it is advantageous that the filtrate inlet port (229) is located at a higher position than the scum outlet port (221) at the lower stationary section of the extraction column.

Meanwhile, the side filtering may be conducted using a filter that can sufficiently remove scum from the raffinate solution discharged through the side stream of the extraction column (200), and the method or the construction of the filter are not specifically limited. However, according to one embodiment, the side filtering may be conducted using a filter having pores with an average diameter of 50 μm or less, or 0.1 to 30 μm, or 0.5 to 20 μm, or 0.5 to 10 μm. Namely, for sufficient removal of scum, it is advantageous that the filter used for the side filtering has pores with an average diameter of 50 μm or less. However, considering filtering efficiency, process flow, and the like, it is advantageous that the filter has pores with an average diameter of 0.1 μm or more.

Further, it is preferable that the filter used for the side filtering is made of a material that is resistant to an extraction solvent and (meth)acrylic acid, and for example, it may be made of cotton, a metal such as SUS (steel use stainless), and the like.

Besides the side filtering, the method of continuous recovery of (meth)acrylic acid may further include a step of filtering the raffinate solution obtained through the lower outlet of the extraction column (200) in each embodiment according to FIG. 1 and FIG. 2 (lower filtering), as shown in FIG. 4 and FIG. 5.

As the above-explained side filtering is used, scum may not substantially exist in the raffinate solution obtained through the lower outlet of the extraction column (200). However, in order to more completely remove scum that can be included, if necessary, the lower filtering may be further conducted. Herein, the description 'not substantially exist' means that the amount of scum included in the raffinate solution obtained through the lower outlet of the extraction column (200) is 5 wt % or less, or 3 wt % or less, or 1 wt % or less, or 0.1 wt % or less, and in which the influence of scum on the stability of process operation is insignificant.

The lower filtering may be conducted using a filter that can sufficiently remove scum included in the raffinate solution discharged from the extraction column (200), and the filtering method and the construction of the filter are not specifically limited. However, according to one embodiment, the lower part filtering may be conducted using a filter having pores with an average diameter of 10 μm or less, or 0.1 to 10 μm, or 0.5 to 10 μm. Further, since the extraction solvent does not substantially exist in the raffinate solution obtained through the lower outlet of the extraction column (200), it is preferable that a filter used for the lower part filtering may be made of material having resistance to (meth)acrylic acid and the like, and as a non-limiting example, the filter may be made of a polymer, cotton, or a metal such as SUS (steel use stainless).

The filtrate obtained through the lower filtering may be recycled to the absorption process and used as an absorption solvent of (meth)acrylic acid.

The side filtering system (220) and the lower filtering system (250) may respectively include at least one filter fulfilling the above requirements, and preferably, they may have a construction including two or more filters having pores with different average diameters connected in series.

Meanwhile, it is preferable that the extraction solvent fed to the extraction column (200) may have solubility and hydrophobicity to (meth)acrylic acid. Further, considering the kind of solvent and the properties required in the subsequent distillation process, it is preferable that the extraction solvent may have a lower boiling point that (meth)acrylic acid. According to one embodiment of the invention, it is advantageous for process operation that the extraction solvent may be a hydrophobic solvent having a boiling point of 120° C. or less, or 10 to 120° C., or 50 to 120° C.

Specifically, the extraction solvent may be at least one selected from the group consisting of benzene, toluene, xylene, n-heptane, cycloheptane, cycloheptene, 1-heptene, ethyl-benzene, methyl-cyclohexane, n-butyl acetate, isobutyl acetate, isobutyl acrylate, n-propyl acetate, isopropyl acetate, methyl isobutyl ketone, 2-methyl-1-heptene, 6-methyl-1-heptene, 4-methyl-1-heptene, 2-ethyl-1-hexene, ethylcyclopentane, 2-methyl-1-hexene, 2,3-dimethylpentane, 5-methyl-1-hexene, and isopropyl-butyl-ether.

Further, the feed amount of the extraction solvent may be controlled such that the weight ratio of the (meth)acrylic acid aqueous solution and the extraction solvent fed to the extraction column (200) may be 1:1 to 1:2, or 1:1.0 to 1:1.8, or 1:1.1 to 1:1.5, or 1:1.1 to 1:1.3. Namely, in order to secure appropriate extraction efficiency, it is preferable that the weight ratio of the (meth)acrylic acid aqueous solution and the extraction solvent fed to the extraction column (200) is maintained 1:1 or more. If the weight ratio exceeds 1:2, although extraction efficiency may be good, loss of (meth) acrylic acid at the distillation column (300) of the subsequent process may increase, and reflux of an azeotropic solvent for blocking it may excessively increase, which is not preferable.

According to one embodiment of the invention, it is favorable for securing extraction efficiency that the temperature of the (meth)acrylic acid aqueous solution fed to the extraction column (200) may be 10 to 70° C.

As the extraction column (200), common extraction columns of a liquid-liquid contact type may be used without specific limitations. As non-limiting examples, the extraction column (200) may be a Karr-type reciprocating plate column, a rotary-disk contactor, a Scheibel column, a Kuhni column, a spray extraction tower, a packed extraction tower, a pulsed packed column, and the like.

Through the extraction process, a (meth)acrylic acid extract solution is discharged to the upper part of the extraction column (200), and the discharged extract solution is fed to the distillation column (300) through a transfer line (203). Further, a raffinate solution is discharged to the lower part of the extraction column (200), and the discharged raffinate solution may be filtered through a lower filtering system (250) as necessary, and then recycled to the (meth) acrylic acid absorption tower (100) through a transfer line (201).

Herein, in the extract solution, in addition to a desired compound (meth)acrylic acid, an extraction solvent, water, and organic by-products may be included. As non-limiting examples, at a steady state where stable operation is conducted, 30 to 40 wt % of (meth)acrylic acid, 55 to 65 wt % of an extraction solvent, 1 to 5 wt % of water, and a remaining amount of organic by-products may be included in the extract solution. Namely, most water included in the (meth)acrylic acid aqueous solution (for example, 85 wt % or more of water included in the aqueous solution) may be recovered as a raffinate solution through the extraction process.

As most water is recovered from the extraction column (200), the distillation load of the distillation column (300) may be reduced to lower energy consumption. Further, since distillation conditions may be relaxed, polymerization of (meth)acrylic acid may be minimized in the distillation process, thus securing operation stability and improving recovery efficiency of (meth)acrylic acid.

In the raffinate solution discharged from the extraction column (200), non-extracted (meth)acrylic acid may be included. However, according to one embodiment of the invention, 5 wt % or less, or 0.5 to 5 wt %, or 1 to 3 wt % of (meth)acrylic acid may be included in the raffinate solution, thus minimizing the loss of (meth)acrylic acid in the absorption process and extraction process.

(Distillation Process)

A distillation process wherein a feed including the (meth) acrylic acid extract solution is distilled to obtain (meth) acrylic acid is conducted.

According to one embodiment of the invention, the feed may be a (meth)acrylic acid extract solution fed from the above-explained extraction process. In this case, the feed is fed to the distillation column (300) through the (meth) acrylic acid extract solution transfer line (203), as shown in FIG. 1.

According to another embodiment, the feed may be a mixture of the (meth)acrylic acid aqueous solution fed from the above-explained absorption process and the (meth) acrylic acid extract solution fed from the above-explained extraction process. In this case, the feed may be simultaneously fed to a distillation column (300) through the (meth) acrylic acid aqueous solution transfer line (103) and the (meth)acrylic acid extract solution transfer line (203), as shown in FIG. 2.

Herein, for effective distillation, it is advantageous that a feed point to which the feed is supplied may be a central part of the distillation column (300), and preferably, it may be any one point corresponding to 40 to 60% of total stages from the uppermost stage of the distillation column (300).

As the feed supplied to the distillation column (300) contacts an azeotropic solvent introduced into the upper part of the distillation column (300), and is heated to an optimum temperature, distillation by evaporation and condensation is achieved.

Herein, in order to effectively separate (meth)acrylic acid included in the feed from the remaining components (for example, water, acetic acid, extraction solvents, and the like), the distillation is preferably conducted by azeotropic distillation.

A solvent used for the azeotropic distillation is preferably a hydrophobic azeotropic solvent that may form an azeotrope with water and acetic acid, and may not form an azeotrope with (meth)acrylic acid. Further, the hydrophobic azeotropic solvent preferably has a lower boiling point than (meth)acrylic acid (for example, a boiling point of 120° C. or less, or 10 to 120° C., or 50 to 120° C.).

Specifically, the hydrophobic azeotropic solvent may be at least one selected from the group consisting of benzene, toluene, xylene, n-heptane, cycloheptane, cycloheptene, 1-heptene, ethyl-benzene, methyl-cyclohexane, n-butyl acetate, isobutyl acetate, isobutyl acrylate, n-propyl acetate, isopropyl acetate, methyl isobutyl ketone, 2-methyl-1-heptene, 6-methyl-1-heptene, 4-methyl-1-heptene, 2-ethyl-1-hexene, ethylcyclopentane, 2-methyl-1-hexene, 2,3-dimethylpentane, 5-methyl-1-hexene, and isopropyl-butyl-ether.

Particularly, in case the extraction process is introduced as in FIG. 1 and FIG. 2, considering production efficiency according to a continuous process, it is preferable that the hydrophobic azeotropic solvent is identical to the extraction solvent of the extraction process. As such, if the same kind of solvents are used in the extraction process and the distillation process, at least a part of the solvent that is distilled in the distillation column (300) and recovered through a phase separation tank (350) may be fed to the (meth)acrylic acid extraction column (200) and reused as an extraction solvent.

Through the distillation process, among the feed, components other than (meth)acrylic acid are discharged to the upper part of the distillation column (300) together with the azeotropic solvent, and (meth)acrylic acid is discharged to the lower part of the distillation column (300).

The upper discharged solution of the distillation column (300) may be fed to the phase separation tank (350) and reused after a predetermined treatment. Herein, the phase separation tank (350) is an apparatus for separating immiscible liquids by gravity or centrifugal force and the like, wherein a relatively light liquid (for example, an organic phase) may be recovered from the upper part of the phase separation tank (350) and a relatively heavy liquid (for example, an aqueous phase) may be recovered from the lower part of the phase separation tank (350).

For example, the upper discharged solution of the distillation column (300) may be separated into an organic phase including an azeotropic solvent and an aqueous phase including water in the phase separation tank (350). Further, the filtrate obtained through filtering of the raffinate solution in the above-explained extraction process may be fed to the phase separation tank (350) through a filtrate transfer line (253) and phase separated together with the upper discharged solution of the distillation column (300). The separated organic phase may be fed to the upper part of the distillation column (300) and used as an azeotropic solvent, and if necessary, at least a part of the organic phase may be fed to the extraction column (200) and used as an extraction solvent.

At least a part of the aqueous phase separated in the phase separation tank (350) may be fed to the (meth)acrylic acid absorption tower (100) and used as an absorption solvent, and a part thereof may be treated as waste water. In the aqueous phase, acetic acid may be partly included, and the concentration of acetic acid included in the aqueous phase may vary according to the kind of azeotropic solvents and reflux ratio and the like. As non-limiting examples, the concentration of acetic acid included in the aqueous phase may be 1 to 50 wt %, or 2 to 40 wt %, or 3 to 30 wt %.

Meanwhile, while the (meth)acrylic acid aqueous solution passes through the (meth)acrylic acid absorption tower (100), extraction column (200), distillation column (300), and the like, at least a part of (meth)acrylic acid included in the aqueous solution may form dimers or oligomers. To minimize such polymerization of (meth)acrylic acid, common polymerization inhibitors may be added to the distillation column (300).

In the lower discharged solution of the distillation column (300), in addition to (meth)acrylic acid, heavies such as a polymer of (meth)acrylic acid, polymerization inhibitors, and the like may be included. Thus, if necessary, a step of feeding the lower discharged solution of the distillation column (300) to a heavies separation tower (400) and separating heavies included in the lower discharged solution may be further conducted. Crude (meth)acrylic acid (CAA) recovered through the process may be passed through an additional crystallization process and obtained as high purity (meth)acrylic acid (HPAA). Herein, the heavies separation process and the crystallization process and the like may be conducted under common conditions, and the process conditions are not specifically limited.

Meanwhile, in the method of continuous recovery of (meth)acrylic acid, each above-explained step may be conducted organically and continuously. Further, in addition to the above-explained steps, processes that can be commonly conducted before or after or simultaneously with each step may be further included.

II. An Apparatus for Continuous Recovery of (Meth)Acrylic Acid

According to another embodiment of the invention, as shown in FIGS. 1 to 3, an apparatus for continuous recovery of (meth)acrylic acid is provided, including:

a (meth)acrylic acid absorption tower (100) equipped with a mixed gas inlet to which a mixed gas including (meth)acrylic acid, organic by-products, and vapor, which is produced by a synthesis reaction of (meth)acrylic acid, is fed, and a (meth)acrylic acid aqueous solution outlet from which a (meth)acrylic acid aqueous solution obtained by contact of the mixed gas with water is discharged;

a (meth)acrylic acid extraction column (200) equipped with a (meth)acrylic acid aqueous solution inlet connected with the (meth)acrylic acid aqueous solution outlet of the absorption tower (100) through an aqueous solution transfer line (102), an extract outlet from which the (meth)acrylic acid extract obtained by contact of the inflowed (meth)acrylic acid aqueous solution with an extraction solvent is discharged, a lower stationary section in which a raffinate solution obtained by contact of the (meth)acrylic aqueous solution with an extraction solvent remains stationary, a raffinate outlet from which the raffinate solution passing through the lower stationary section is discharged, a scum outlet port where at least a part of the raffinate solution containing scum is discharged through a side stream equipped at any one point of the lower stationary section, and a filtrate inlet port formed such that a filtrate obtained through filtering of the raffinate solution discharged from the scum outlet port is inflowed through a side stream equipped at any other point of the lower stationary section;

a side filtering system (220) equipped with a raffinate inlet connected with the scum outlet port of the extraction column (200), into which the raffinate containing scum is inflowed, a filter for filtering the inflowed raffinate solution, a scum outlet from which the scum separated from the raffinate solution by filtering is discharged, and a filtrate outlet connected such that the filtrate is fed to the filtrate inlet port of the extraction column; and a distillation column (300) equipped with an extract inlet connected with the extract outlet of the extraction column (200) through an extract transfer line (203), and a (meth)acrylic acid outlet from which (meth)acrylic acid obtained by distillation of a feed containing the inflowed extract solution is discharged.

According to yet another embodiment, as shown in FIGS. 2 and 3, the distillation column (300) is equipped with a (meth)acrylic acid aqueous solution inlet connected with the (meth)acrylic acid aqueous solution outlet of the absorption tower (100) through an aqueous solution transfer line (103), an extract inlet connected with the extract outlet of the extraction column (200) through an extract transfer line (203), and a (meth)acrylic acid outlet from which (meth)acrylic acid obtained by distillation of the inflowed (meth)acrylic acid aqueous solution and a feed containing an extract solution is discharged; and the apparatus is operated such that a part of the (meth)acrylic acid aqueous solution discharged from the absorption tower (100) is fed to the (meth)acrylic acid aqueous solution inlet of the extraction column (200) through the aqueous solution transfer line (102), and the remainder of the (meth)

acrylic acid aqueous solution discharged from the absorption tower (100) is fed to the (meth)acrylic acid aqueous solution inlet of the distillation column (300) through the aqueous solution transfer line (103).

The apparatus for continuous recovery of (meth)acrylic acid according to the above embodiments may be operated according to the above-explained method for continuous recovery of (meth)acrylic acid.

Particularly, it is preferable that the scum outlet port and the filtrate inlet port of the extraction column (200) are formed such that the outflow direction of the raffinate solution and the inflow direction of the filtrate through the side streams are opposite to each other. Namely, compared to the case wherein the scum outlet port (221) and the filtrate inlet port (229) of the extraction column (200) make an angle of 180° as shown in the right drawing of FIG. 3 (*a*), the case wherein the angle is less than 180°, less than 135°, or less than 90°, or less than 45°, or 0° as shown in the right drawing of FIG. 3 (*b*) may be favorable for smooth discharge of scum.

Herein, considering that an organic phase and an aqueous phase may be included in the discharged substance through the scum outlet port (221) and the introduced substance through the filtrate inlet port (229), and for smooth phase separation of the organic phase and the aqueous phase in the lower stationary section of the extraction column, it is advantageous that the filtrate inlet port (229) is located at a higher position than the scum outlet port (221) at the lower stationary section of the extraction column.

Further, it is preferable that the side filtering system (220) is equipped with a filter having pores with an average diameter of 50 μm or less, or 0.1 to 30 μm, or 0.5 to 20 μm, or 0.5 to 10 μm, so as to sufficiently remove scum from the raffinate solution discharged through the side stream of the extraction column (200). It is also preferable that the filter of the side filtering system (220) is made of a material that is resistant to an extraction solvent and (meth)acrylic acid, and for example, it may be made of cotton, a metal such as SUS (steel use stainless), and the like.

Meanwhile, as shown in FIG. 4 and FIG. 5, the apparatus of each embodiment according to FIG. 1 and FIG. 2 may be further equipped with a lower filtering system equipped with a raffinate inlet connected with the raffinate outlet of the extraction column (200), into which the raffinate solution is inflowed, a filter for filtering the inflowed raffinate solution, and a filtrate outlet from which a filtrate obtained by filtering is discharged. It is preferable that the lower filtering system (250) is equipped with a filter having pores with an average diameter of 10 μm or less, or 0.1 to 10 μm, or 0.5 to 10 μm.

In addition, since extraction solvents do not substantially exist in the raffinate solution obtained through the lower outlet of the extraction column (200), it is preferable that the filter of the lower filtering system (250) is made of a material that is resistant to (meth)acrylic acid, and for example, it may be made of polymer such as polypropylene, cotton, a metal such SUS (steel use stainless), and the like.

Meanwhile, the (meth)acrylic acid absorption tower (100) may be a packed tower or a multistage tray tower for improving contact efficiency of the (meth)acrylic acid-containing mixed gas (1) with an absorption solvent. Inside of the packed tower, fillers such as a Raschig ring, a pall ring, a saddle, gauze, structured packing, and the like may be applied.

As the (meth)acrylic acid extraction column (200), common extraction columns of a liquid-liquid contact type may be used without specific limitation. As non-limiting examples, the extraction column may be a Karr-type reciprocating plate column, a rotary-disk contactor, a Scheibel column, a Kuhni column, a spray extraction column, a packed extraction tower, a pulsed packed column, and the like.

The distillation column (300) may be a packed column including fillers inside or a multistage column, preferably a sieve tray column or a dual flow tray column, and the like.

In addition, the acetic acid absorption tower (150), (meth)acrylic acid aqueous solution transfer line (102), extract transfer line (203), phase separation tank (350), heavies separation tower (400), and the like may have constructions common in the technical field to which the invention pertains.

Hereinafter, preferable examples are presented to aid in understanding of the invention. However, these examples are only to illustrate the invention, and the scope of the invention is not limited thereto.

Comparative Example

A Scheibel type of extraction column with an extraction part of a total of 72 stages, a column inner diameter of 32 inches, and a column height of 545 inches was prepared. Into the feed inlet of the extraction column, an acrylic acid aqueous solution (acrylic acid concentration of about 65.5 wt %, acetic acid concentration of about 2.25 wt %) was fed, and into the extraction solvent inlet of the extraction column, toluene (acrylic acid concentration of about 0.18 wt %) was fed. Herein, the weight ratio of the acrylic acid aqueous solution to toluene fed to the extraction column was fixed to about 1:1.3.

At the lower part of the extraction part from which a raffinate solution was discharged, a lower filter system including a metal mesh filter having pores with an average diameter of about 20 μm and a metal mesh filter having pores with an average diameter of about 1 μm connected in series was installed, and using the same, scum included in the raffinate solution discharged to the lower part was removed.

Herein, the input of the acrylic acid aqueous solution was controlled to 5.3 ton/h, and the input of toluene was controlled to about 6.89 ton/h. Further, the discharge mass flow of the raffinate solution was maintained at about 1.55 ton/h so that the interface between an organic phase and an aqueous phase formed by the raffinate solution that remains stationary at the lower part of the extraction column may be maintained at a constant level, and the discharge mass flow of the extract solution was about 10.64 ton/h.

Under a maximum mechanical reciprocating speed of the porous plate (namely, maximum rpm immediately before generating flooding) enabling realization of a maximum acrylic acid extraction rate in the extraction column, acrylic acid concentration in the raffinate solution was analyzed.

As the result, at the beginning of operation, the concentration of acrylic acid in the raffinate solution consisting of an aqueous phase was about 1.65 wt %, and the concentration of toluene was about 820 ppm. However, after about 24 h of operation, the concentration of acrylic acid in the raffinate solution increased to about 4.2 wt %, and the concentration of toluene increased to about 6.5 wt %. This is because the amount of scum accumulated at the interface between the organic phase and the aqueous phase increases (the thickness of a scum layer increases), and the organic phase and the aqueous phase exist together in the form of emulsion in the scum and are discharged together to the lower part of the extraction column.

Herein, although the raffinate solution discharged from the lower part of the extraction column passed through the lower filtering system connected to the extraction column to remove scum, the concentration of acrylic acid was high, and due to a high concentration of toluene, the raffinate solution could not be fed as an absorption water of the acrylic acid absorption process.

Further, as the operation of the extraction column continued, scum was accumulated toward the organic phase (namely, to the internal direction of the extraction column) at the interface between the organic phase and the aqueous phase of the lower stationary section of the extraction column. Due to the accumulation of scum, the extraction column was contaminated, extraction efficiency gradually decreased, and finally, the operation of the extraction column was stopped.

Example

At the lower stage of an extraction column from which a raffinate solution is discharged, a lower filtering system equipped with a metal mesh filter having pores with an average diameter of about 1 μm was installed. Further, a side filtering system equipped with a metal mesh filter having pores with an average diameter of about 20 μm was installed so as to be connected with the side stream of the extraction column, as shown in FIG. 3 (b).

As such, except that the above lower filtering system and side filtering system were installed, the extraction process was progressed by the same method as the comparative example. Herein, the mass flow of the raffinate solution passing through the side filtering system was controlled to about 1.5 to 5 ton/h.

As the result, at the beginning of the operation, the concentration of acrylic acid in the raffinate solution consisting of an aqueous phase was about 1.64 wt %, and the concentration of toluene was about 620 ppm. Further, even after the operation time elapsed, the concentrations of acrylic acid and toluene in the raffinate solution were maintained at the initial values.

The differential pressure of the side filtering system increased as the operation time of the extraction column elapsed, and after about 2 days to 3 days of operation, maximum differential pressure limit was reached, and after removing scum by backwashing, the side filtering system was reused. Further, the differential pressure of the lower filtering system increased very slowly, and after about 8 to 10 days of operation, maximum differential pressure limit was reached, and after removing scum by backwashing, the lower filtering system was reused.

As explained, by using the side filtering system, accumulation of scum inside the extraction column could be prevented, and the extraction process could be operated for more than 3 months without contamination of the extraction column and a decrease in extraction efficiency due to scum.

The invention claimed is:

1. A method of continuous recovery of (meth)acrylic acid, comprising:
an extraction process wherein a (meth)acrylic acid aqueous solution is contacted with an extraction solvent in an extraction column to obtain a (meth)acrylic acid extract solution through an upper outlet of the extraction column and a raffinate solution passing through a lower stationary section of the extraction column through the lower outlet; and
a distillation process wherein a feed containing the (meth) acrylic acid extract solution is distilled to obtain (meth) acrylic acid,
wherein the raffinate solution containing scum that is accumulated at an interface between an organic phase and an aqueous phase formed by phase separation of the raffinate solution in the lower stationary section of the extraction column is discharged through a side stream located at any one point of the lower stationary section and filtered, and a filtrate is inflowed through a side stream located at any other point of the lower stationary section.

2. The method according to claim 1, wherein the extraction process is conducted such that the interface between the organic phase and the aqueous phase formed by phase separation of the raffinate solution is formed at the side stream located at any one point of the lower stationary section of the extraction column.

3. The method according to claim 1, wherein discharging of the raffinate solution containing scum and filtering through the side streams of the extraction column are conducted continuously or discontinuously.

4. The method according to claim 1, wherein the outflow direction of the raffinate solution containing scum through the side stream of the extraction column and the inflow direction of the filtrate through the side stream of the extraction column are opposite to each other.

5. The method according to claim 1, wherein the filtering is conducted using a filter having pores with an average diameter of 50 μm or less.

6. The method according to claim 1, wherein the method further comprises:
an absorption process wherein a mixed gas including (meth)acrylic acid, organic by-products, and water vapor, which is produced by a synthesis reaction of (meth)acrylic acid, is contacted with an absorption solvent including water to obtain a (meth)acrylic acid aqueous solution; and
the extraction process is carried out on the (meth)acrylic acid aqueous solution obtained through the absorption process; and
the distillation process is carried out on a feed containing the (meth)acrylic acid extract solution obtained through the extraction process to obtain (meth)acrylic acid.

7. The method according to claim 1, wherein the method further comprises:
an absorption process wherein a mixed gas including (meth)acrylic acid, organic by-products, and water vapor, which is produced by a synthesis reaction of (meth)acrylic acid, is contacted with an absorption solvent including water to obtain a (meth)acrylic acid aqueous solution; and
the extraction process is carried out on a part of the (meth)acrylic acid aqueous solution obtained through the absorption process; and
the distillation process is carried out on a feed containing the remainder of the (meth) acrylic acid aqueous solution obtained through the absorption process and the (meth)acrylic acid extract obtained through the extraction process to obtain (meth)acrylic acid.

8. The method according to claim 6, further comprising a step of filtering the raffinate solution obtained through the lower outlet of the extraction column.

9. The method according to claim 8, wherein the filtering of the raffinate solution obtained through the lower outlet of the extraction column is conducted using a filter having pores with an average diameter of 10 μm or less.

10. The method according to claim 8, wherein the filtrate obtained through the filtering is recycled to the absorption process and used as the absorption solvent.

\* \* \* \* \*